United States Patent [19]

Marin et al.

[11] Patent Number: 5,443,477

[45] Date of Patent: Aug. 22, 1995

[54] APPARATUS AND METHOD FOR DEPLOYMENT OF RADIALLY EXPANDABLE STENTS BY A MECHANICAL LINKAGE

[75] Inventors: Michael L. Marin; Ralph Marin, both of New York, N.Y.

[73] Assignee: Stentco, Inc., Cross River, N.Y.

[21] Appl. No.: 196,278

[22] Filed: Feb. 10, 1994

[51] Int. Cl.⁶ .............................................. A61M 29/00
[52] U.S. Cl. ........................................ 606/198; 623/1; 604/106
[58] Field of Search ............... 606/152, 108, 153, 191, 606/195, 198, 200; 604/53, 104, 105, 106, 107; 623/1, 11, 12

[56] References Cited

U.S. PATENT DOCUMENTS

| | | |
|---|---|---|
| 832,201 | 10/1906 | Kistler . |
| 1,433,031 | 10/1922 | Pegaitaz . |
| 1,737,488 | 11/1929 | Zohlen . |
| 2,684,069 | 7/1954 | Donaldson et al. . |
| 3,495,586 | 2/1970 | Regenbogen . |
| 3,517,128 | 6/1970 | Hines . |
| 3,557,794 | 1/1971 | Van Patten . |
| 3,704,712 | 7/1972 | Giesy et al. . |
| 3,968,800 | 7/1976 | Vilasi . |
| 3,996,938 | 12/1976 | Clark, III . |
| 4,168,709 | 9/1979 | Bentov . |
| 4,320,762 | 3/1982 | Bentov . |
| 4,566,465 | 1/1986 | Arhan et al. ........................ 606/192 |
| 4,577,631 | 3/1986 | Kreamer . |
| 4,585,000 | 4/1986 | Hershenson . |
| 4,648,402 | 3/1987 | Santos . |
| 4,776,337 | 10/1988 | Palmaz . |
| 4,921,484 | 5/1990 | Hillstead . |
| 4,990,151 | 2/1991 | Wallstén . |
| 5,064,434 | 11/1991 | Haber . |
| 5,074,871 | 12/1991 | Groshong ............................ 623/1 |
| 5,197,978 | 3/1993 | Hess ........................................ 623/1 |
| 5,263,963 | 11/1993 | Garrison et al. . |
| 5,279,565 | 1/1994 | Klein et al. ........................ 604/105 |

Primary Examiner—Stephen C. Pellegrino
Assistant Examiner—William Lewis
Attorney, Agent, or Firm—Darby & Darby

[57] ABSTRACT

The invention provides a method and apparatus for intraluminal delivery and deployment of an expandable prosthesis at a site within a body lumen. The apparatus for intraluminal delivery and deployment includes a support for supporting the expandable prosthesis while being delivered to the site within the body lumen, and a radially displaceable mechanical linkage connected to the support for radially displacing the support. The linkage is adapted to deploy the expandable prosthesis when it is displaced radially outward. The linkage permits continuous fluid flow within the body lumen while the expandable prosthesis is being deployed. The present invention can also be used without stents for expanding a body lumen. The present method comprises the steps of transmitting a radially, outwardly directed displacement force to the support from a control mechanism, the support being displaced radially outwardly to an expanded stance such that the prosthesis contacts the body passageway, and transmitting a radially, inwardly directed displacement force to the support from a control mechanism, the support being displaced radially inwardly to a recoiled stance less than the diameter of the body passageway while leaving the prosthesis in contact the body passageway. Fluid flow is permitted throughout the delivery and deployment process.

45 Claims, 7 Drawing Sheets

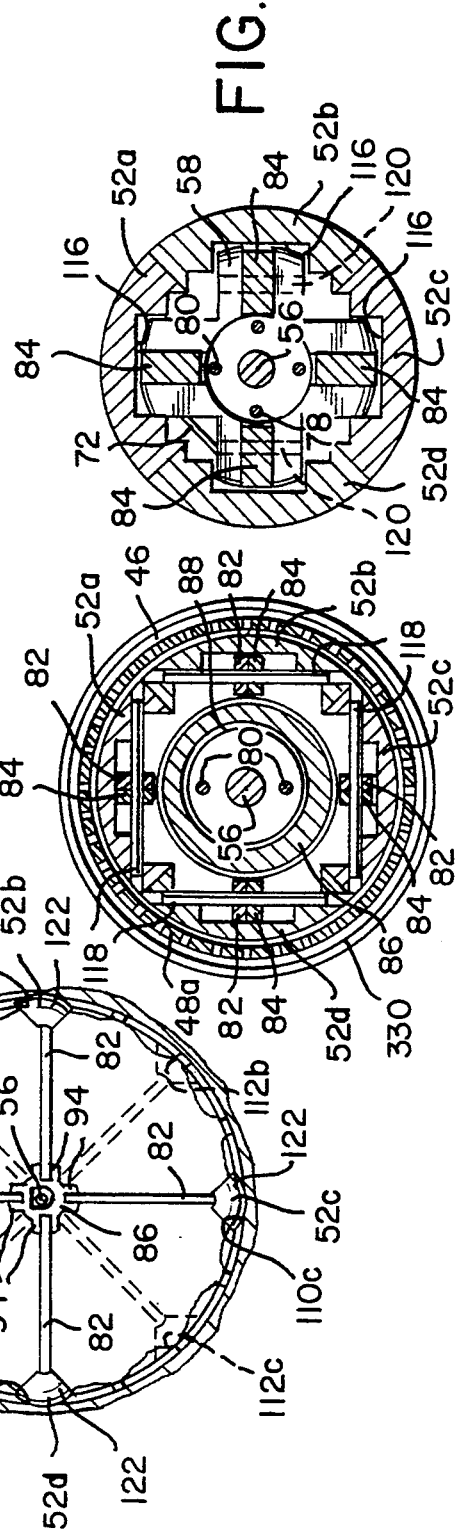
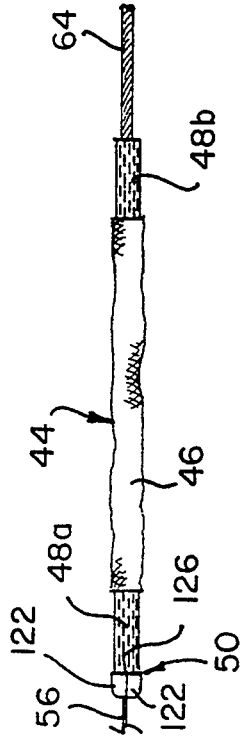
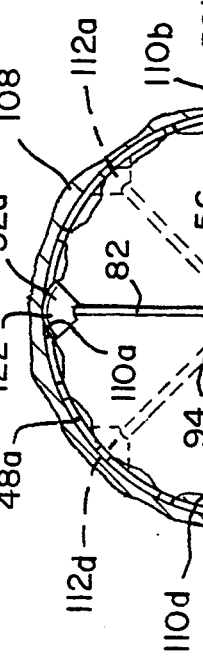
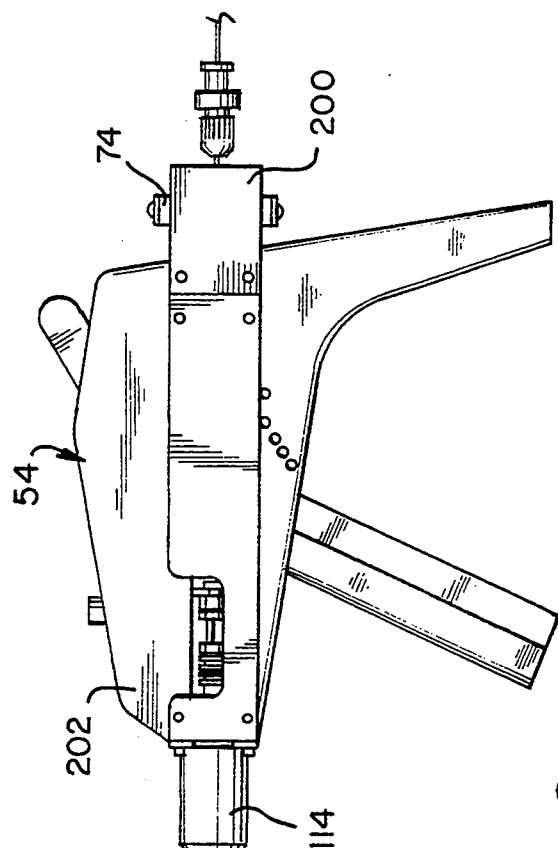
FIG. 1
FIG. 9
FIG. 6
FIG. 8

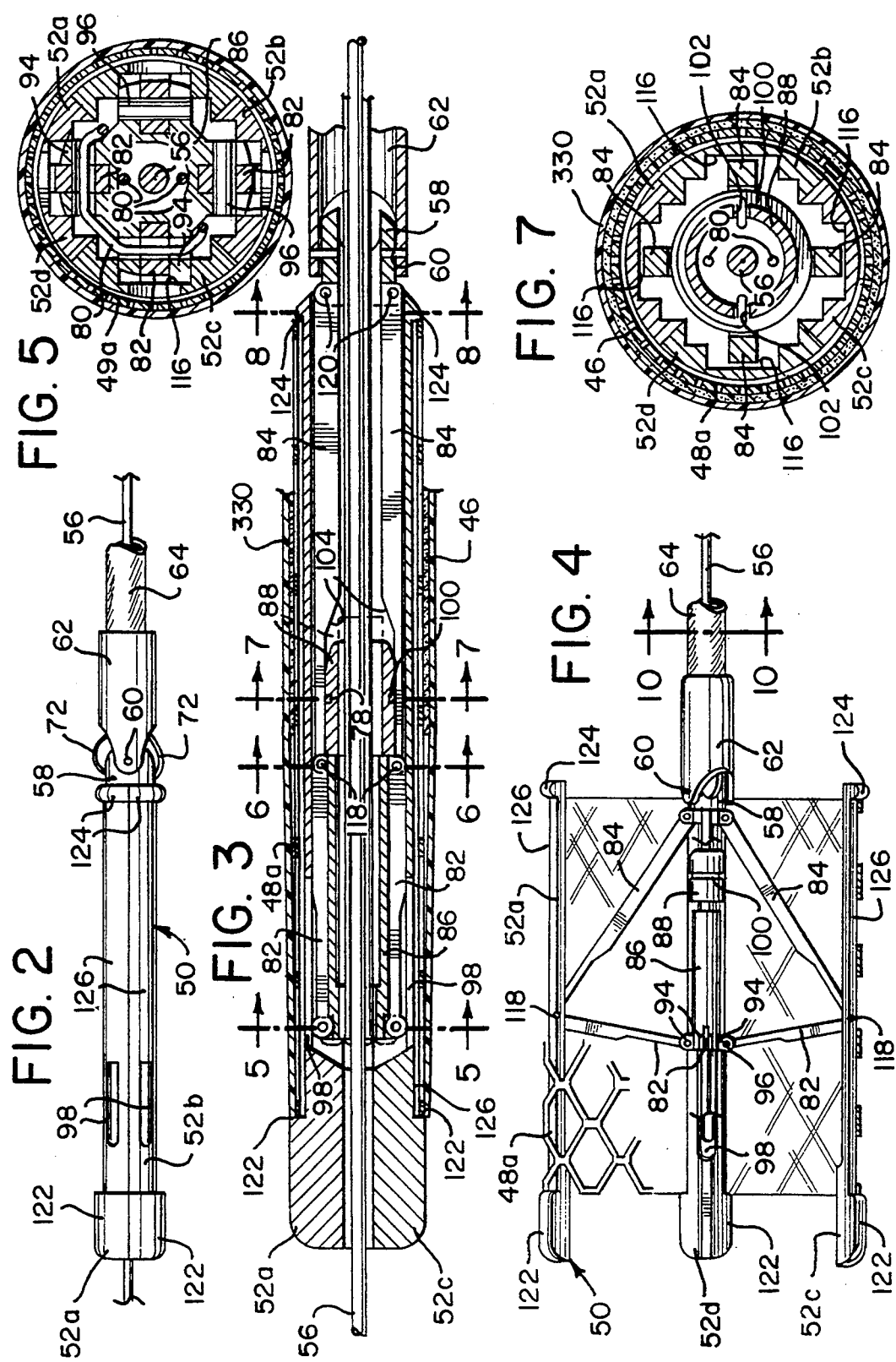

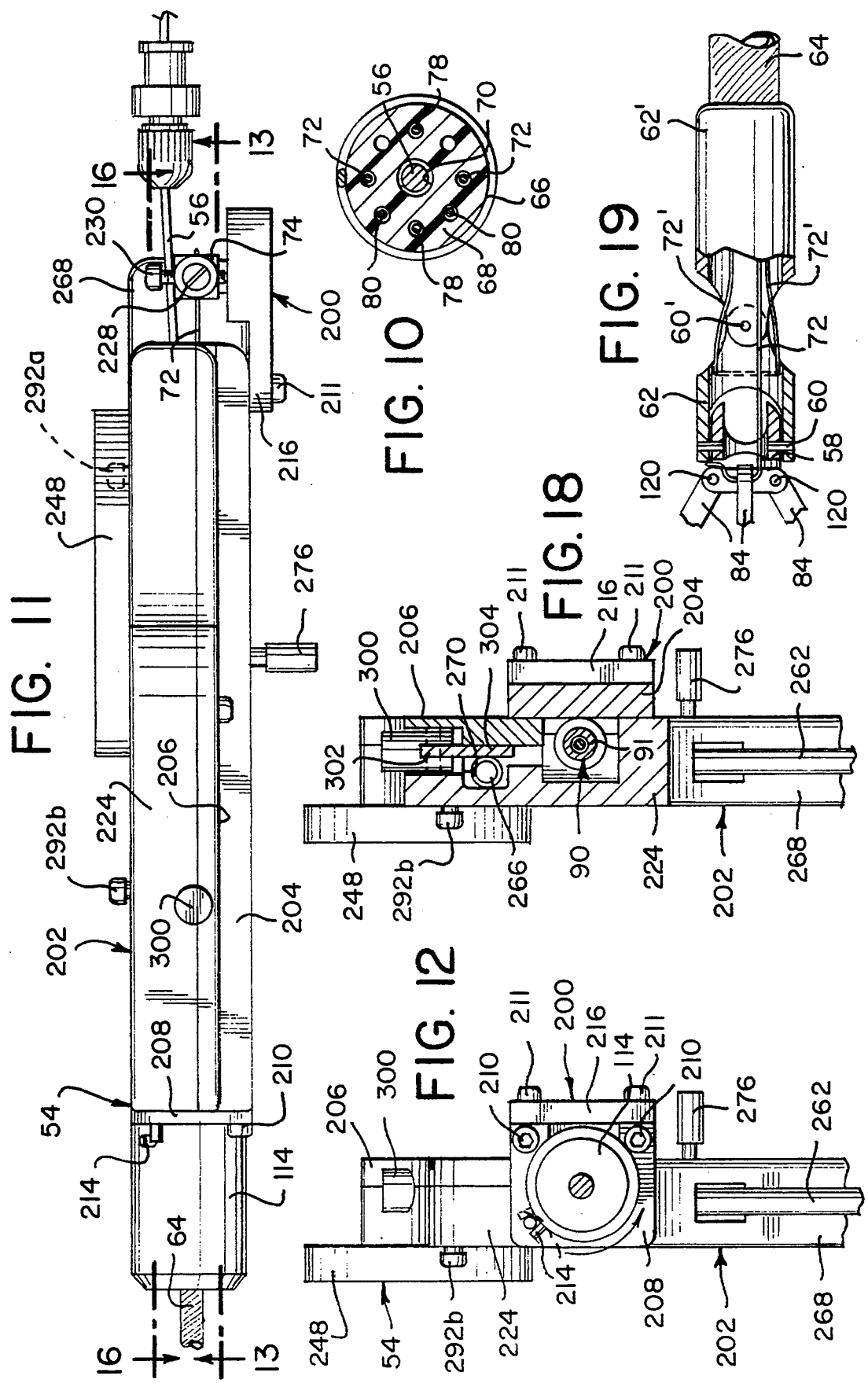

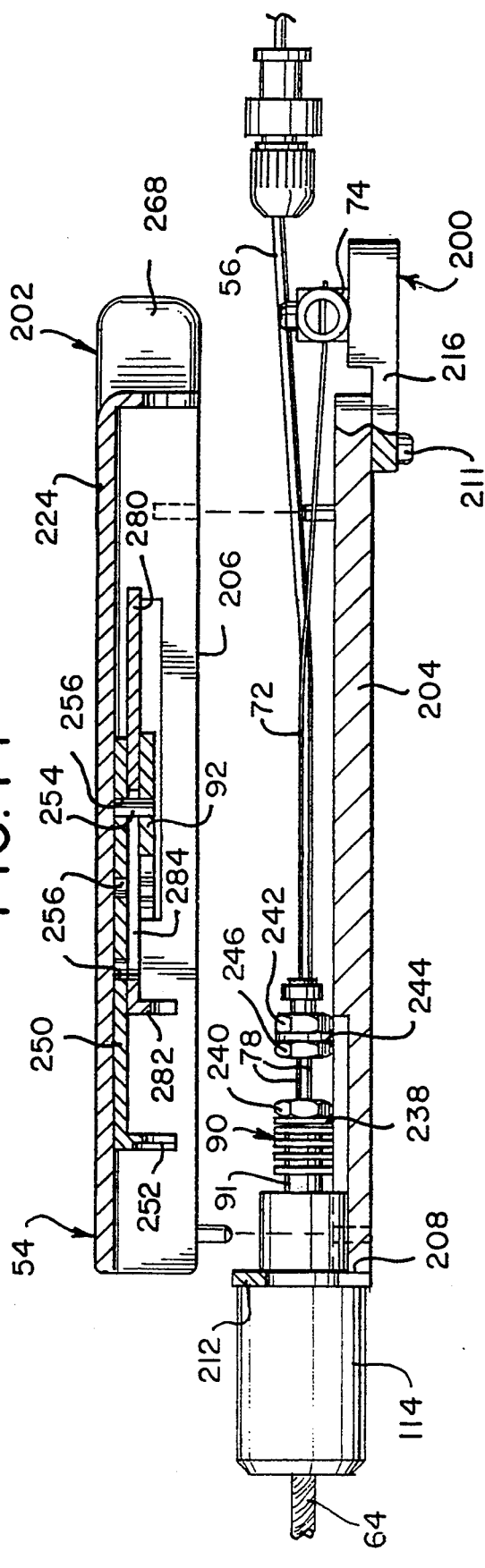
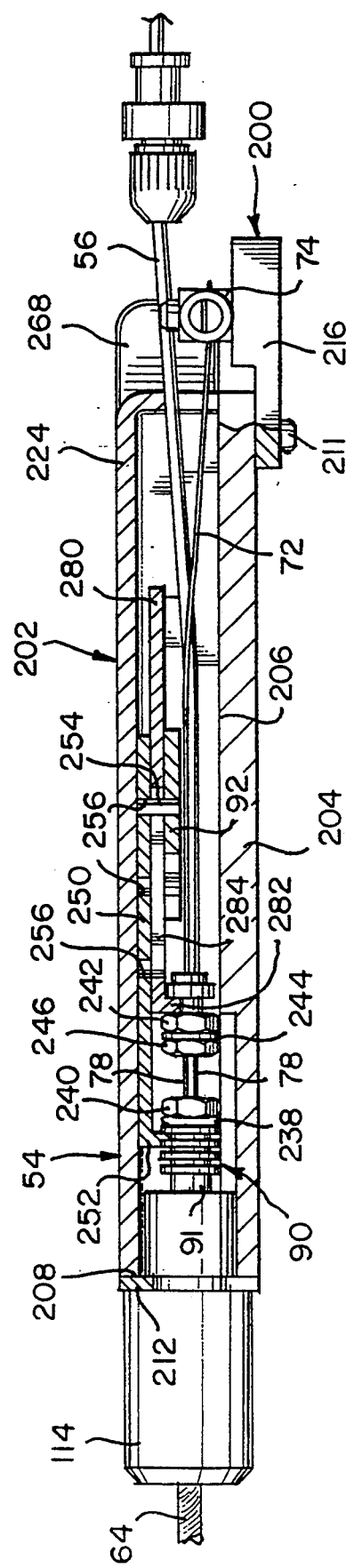
FIG. 14
FIG. 15

APPARATUS AND METHOD FOR DEPLOYMENT OF RADIALLY EXPANDABLE STENTS BY A MECHANICAL LINKAGE

FIELD OF THE INVENTION

This invention relates to an apparatus for deploying radially expandable stents and more particularly to an apparatus that permits continuous vascular fluid flow while intraluminally deploying a radially expandable stent using a mechanical linkage.

BACKGROUND OF THE INVENTION

Cardiovascular disease is effecting an ever increasing proportion of the human population. Diseases of the vascular system may occur as a result of several etiologies which lead to the development of atherosclerosis. Atherosclerotic vascular disease (hardening of the arteries) occurs in two predominant manifestations. In one form, a narrowing of blood vessels impedes blood flow in one or more regions within the vessel lumen. In another form, arterial wall degeneration with a formation of aneurysms causes the wall of the affected artery to weaken and balloon outward by thinning. Management of both narrowed and dilated arteries in the peripheral circulation has come under the domain of vascular surgery.

Investigators in the field of vascular surgery had at one time handled both narrowed and dilated arteries by a technique for suture anastomosis (sewing together) of two arterial segments using needle and thread. A significant advance in the field of vascular surgery, however, was the development of the technique of vascular bypass grafting. Vascular bypass grafting involves the use of either accessory vessel segments or artificial arteries to bridge defects in the vascular system, or to correct narrowing or blockages in affected arteries. This was a significant advance because prior to the implementation of this technique, there existed no significant therapeutic treatment for an individual having an abdominal aortic aneurism, that is, a dilatation of the main artery of the body. Such a patient had to live with the threat of aortic aneurysm rupture and death.

One clinical approach known to vascular surgeons for patients having a large aneurysm in their abdominal aorta is an abdominal aortic aneurysm repair. This repair operation involves a long, abdominal incision extending from the lower border of the breast bone down to the pubic bone so that the abdominal aorta and the aneurysm can be exposed and a prosthetic arterial graft can be implanted. The operation requires a general anesthesia with a breathing tube, extensive intensive care unit monitoring in the immediate post-operative period, along with blood transfusions and stomach and bladder tubes. The operation itself takes approximately six hours and, if no complications occur, the patient can return home within seven to fourteen days after convalescence.

Today, there is a significantly less invasive clinical approach known as endovascular grafting. This procedure involves the use of prosthetic or other vascular grafts in combination with vascular stents, so called "graftstent" combinations. J. C. Parodi et al., *Transfemoral Intraluminal Graft Implantation for Abdominal Aortic Aneurysms*, 5 ANNALS OF VASCULAR SURGERY 491 (1991). Stents are devices which permit fixation of a graft to an arterial wall without sewing. Conventionally, a stent-graft-stent (" graftstent") complex is loaded onto a catheter which is then guided through a body lumen to the general vicinity of an aneurysm. An angioplasty balloon expands the first stent until it bears firmly against the arterial wall, the balloon is then deflated and the catheter is withdrawn so that it can be reloaded or replaced. The catheter is then guided to the second stent so that the second stent can be expanded.

The stent which has had the greatest experimental and clinical application for endovascular surgery is the balloon-expandable Palmaz stent. U.S. Pat. No. 4,776,337. This stent can be reliably and readily affixed to any graft material currently employed for bypass. The Palmaz stent is made of a multiply slotted tubular piece of stainless steel. The slots allow the stent to maintain a small overall diameter prior to use for easy introduction to the appropriate artery and location within the body. Once the stent has reached that location, it may be expanded to the desired diameter using a conventional angioplasty balloon to form a tight friction seal to the artery wall.

Investigators have noted encouraging preliminary results with the endovascular grafting technique; nevertheless, a number of issues have been encountered during the procedure. A significant issue with respect to endovascular grafting techniques concerns the potential shift in location of a graftstent device that is deployed with a conventional angioplasty balloon. Theoretically, a balloon deployed stent can be deployed exactly at the desired site. In fact, a suitably positioned stent can shift, rotate or separate from an angioplasty balloon during the insertion or inflation of the balloon which lends a level of uncertainty to the procedure.

A separate source of concern to surgeons using the Palmaz stent with conventional deployment devices is that the metallic struts of the stent itself can perforate the angioplasty balloon during loading of the graftstent, advancing the graftstent to a designated site within a patient, or deploying the graftstent. Any perforation in the angioplasty balloon will result in inadequate inflation of the balloon which results in either improper deployment of the stent or the need to restart or protract the process. It is the risk of perforation that necessitates the use of hydraulic fluids for filling the angioplasty balloon; if the balloon were filled with air and inadvertently perforated, the risk of embolism would be severe.

Perhaps the most significant issue concerns the rate of deployment of a graftstent complex, especially those larger diameter prostheses for use in the abdominal aortic artery. The rate at which the balloon can be inflated is limited by the size of the catheter inflation lumen and the speed with which fluid can be injected through the catheter and into the angioplasty balloon. The rate at which the balloon can be deflated is similarly impacted.

The rate of inflation and deflation of the angioplasty balloon bears directly on the stress induced on the heart during deployment because the intraluminal fluid pressure upstream of the balloon is increased at all times that the balloon blocks the artery, that is, whenever the balloon is not deflated. This increased fluid pressure occurs in beats, from the heart, which may cause the angioplasty balloon and stent to shift to a position more distal than the surgeon had intended to deploy the stent. In addition, when the balloon is inflated within the abdominal aortic artery, there is a sudden increase in pressure in the artery which could result in heart disfunction. Accordingly, there exists a need to provide more reliable and rapid deployment of graftstents as well as rapid recoil of the deploying means so that blood flow is minimally impeded.

SUMMARY OF THE INVENTION

These and other needs are addressed by the present invention in which an apparatus for intraluminal delivery and deployment of an expandable prosthesis at a site within a body lumen comprises a support for supporting the expandable prosthesis while being delivered to the site within the lumen and a radially displaceable mechanical linkage for radially displacing the support, the linkage expanding the expandable prosthesis on the support when the linkage is displaced radially outward, the linkage permitting continuous fluid flow within the lumen while the expandable prosthesis is being expanded and deployed. In one form, the apparatus may be slid onto a guide wire and comprise an axially moveable member mounted with respect to the guide wire, a deployment wire having a distal end fixedly coupled to the member for axially moving the member with respect to the guide wire, a plurality of wings surrounding the member to form a support surface for the stent, and a linkage for linking the wings to the member, the linkage causing the wings to displace radially outward when the member moves axially with respect to the guide wire in a first direction and displace radially inward when the member moves axially with respect to the guide wire in a second direction. The present invention can also be used without stents for expanding a body lumen.

These and other needs are also addressed by a method for intraluminally implanting a prosthesis disposed on a mechanical support at a distal end of a catheter which has been inserted into a body passageway, according to the present invention, comprising the steps of transmitting a radially, outwardly directed displacement force substantially instantaneously to the support from a control mechanism, the support being displaced radially outwardly to an expanded stance such that the prosthesis contacts the body passageway, and transmitting a radially, inwardly directed displacement force substantially instantaneously to the support from a control mechanism, the support being displaced radially inwardly to a recoiled stance less than the diameter of the body passageway while leaving the prosthesis in contact the body passageway. Advantageously, each of the transmitted displacement forces is calibrated to the displacement of the support such that a prosthesis is expanded to a predetermined diameter.

These and other objects, features and advantages of the present invention will be readily apparent from the following detailed description of the invention taken in conjunction with the accompanying drawings.

BRIEF DESCRIPTION OF DRAWINGS

FIG. 1 is a side view of a prosthesis mounted on an apparatus constructed in accordance with the present invention;

FIG. 2 is a side view of a steerable deployment head of the present invention in a radially recoiled stance;

FIG. 3 is a longitudinal cross-section of a steerable deployment head of the present invention;

FIG. 4 is a side view partially in section of a steerable deployment head of the present invention in a radially displaced stance;

FIG. 5 is a cross-section taken along line 5—5 of FIG. 3;

FIG. 6 is a cross-section taken along line 6—6 of FIG. 3;

FIG. 7 is a cross-section taken along line 7—7 of FIG. 3;

FIG. 8 is a cross-section taken along line 8—8 of FIG. 3;

FIG. 9 is a from view of a steerable deployment head of the present invention within a body lumen which has been suitably radially displaced so as to intraluminally distend and anchor a prosthesis;

FIG. 10 is a cross-section taken along line 10—10 of FIG. 4;

FIG. 11 is a top view of an actuator subassembly and a catheter mounting subassembly in assembled relationship to one another for remotely controlling the deployment head of the present invention;

FIG. 12 is a from view of the assembly of FIG. 11;

FIG. 14 is a cross-section taken along line 14—14 of FIG. 13 showing the catheter mounting subassembly in spaced proximity to the actuator subassembly;

FIG. 15 is a cross-section taken along line 15—15 of FIG. 13 showing the catheter mounting subassembly and the actuator subassembly in abutting relationship to one another;

FIG. 18 is a cross-section taken along the line 18—18 of FIG. 13 showing the catheter mounting subassembly and the actuator subassembly in engaging relationship to one another; and FIG. 19 is side view partially in section of a modified embodiment showing a deployment head of the present invention and its coupling to two articulated members.

DETAILED DESCRIPTION OF THE INVENTION

Figure 13:
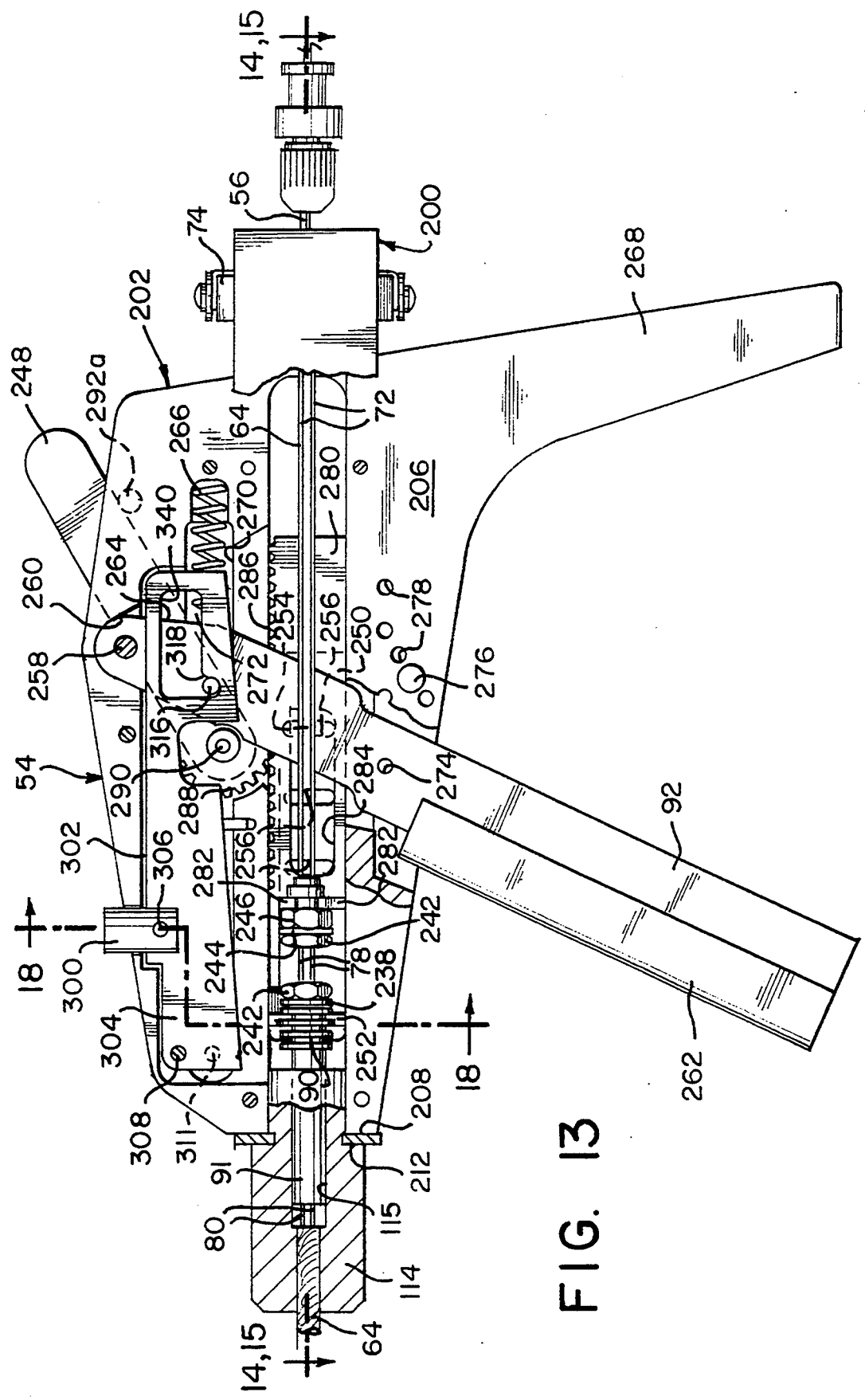
FIG. 13 is a partial cross-section of one side of the assembly taken substantially along line 13—13 of FIG. 11.

By way of overview and introduction, there is seen in FIG. 1 an apparatus for the deployment of a graftstent complex 44. Graftstent complex 44 comprises a thin-walled, crimped, knitted graft 46 of polyester ("DACRON"), expandable PTFE, or similar material which overlaps and is sutured to a pair of stents 48a and 48b. Suitable vascular grafts that may be used include Model 80S07TW by Impra, of Tempe, Ariz.; and Model VT06070L by Gortex, of Flagstaff, Ariz. One stent usable with the present invention is the RM1001 stent manufactured by Stentco, Inc. of Elmwood Park, N.J. Another stent that may be used is the PS30 Palmaz balloon-expandable stent manufactured by Johnson & Johnson Interventional Systems of Warren, N.J. Distal stent 48a is mounted on a head 50 which has a support surface comprised of four radially displaceable wings 52a, 52b, 52c, and 52d (see FIGS. 5 and 9). All of the wings may be the same. The stents may have an unexpanded diameter of five to ten millimeters or less for delivery purposes. At the desired location, the stent on head 50 is radially distended to an expanded diameter by a mechanical linkage actuated by a control mechanism 54, described below. The radial expansion of the stent is continued until it invaginates into an arterial wall and fastens itself by a friction seal, as also described below.

In accordance with a broad object of this invention, stents 48a and 48b are advanced to a designated site within a patient's vascular system under fluoroscopic control in conventional manner by sliding the device relative to a separately inserted guide wire 56. Head 50 includes an annular support 58 (FIGS. 2 and 3) that is mounted at a proximal face by a pin 60 to a first ferrule 62. Ferrule 62 is press fit onto the distal end of an elongate flexible shaft 64. Pin 60 enables head 50 to pivot with respect to shaft 64. Shaft 64 comprises a wire wound coil 66 (FIG. 10) surrounding a multilumen plastic catheter 68. Catheter 68 includes a central lumen 70 that receives the proximal end of the guide wire such as when head 50 is advanced to the designated site within a patient. The proximal end of shaft 64 is retained with a nose cone 114. The catheter includes various lumens (not numbered) for receiving the control wires as described below. The guide wire is used in conventional fashion to guide the gratistent complex 44 through the patient's vascular system. Guide wire 56 is preferably at least 0.025 inches in diameter, and may be 0.035 inches or more. The guide wire may be of tempered stainless steel and is conventionally covered with a synthetic material, such as TEFLON.

In FIGS. 2 and 19, a taut steering wire 72 is shown looped at its distal end through suitable holes in the arms 84 and bifurcated lugs 106 at the distal end of annular support 58 on transverse sides of pin 60. By means of a steering lever 74 at the proximal end of the steering wire, head 50 may be manually manipulated within the patient's vascular system to facilitate advancement of the device and the deployment of the stent in an angulated arterial segment. The steerability of head 50 about pin 60 aids the surgeon in negotiating the tortious or twisty arteries in the patient's vascular system. Preferably, head 50 is free to pivot 30° about first ferrule 62. Steering wire 72 is housed in an additional lumen within multilumen catheter 68 along with initiator and deployment wires 78,80 which are used for operating head 50, as shown in FIG. 10. Preferably, steering wire 72 is 0.010 inches in diameter or less.

Referring now to FIG. 3, the apparatus of the present invention deploys the stent by radially displacing the wings through a mechanical coupling which consists of four pairs of arms 82, 84, each pair associated with each wing, together with a tubular slide 86 and an initiator 88, both of which are axially slideably mounted with respect to the guide wire and are commonly associated with each of the wings. The distal ends of two of the arms 82 are pivotally attached to the distal end of slide 86 by deployment wire 80 (FIG. 5) which extends from the control mechanism 54 through shaft 64 and is looped at its distal end through suitable holes in the arms 82 and bifurcated lugs 94 at the distal end of slide 86. The distal ends of the other two arms 82 are pivotally attached to the distal end of slide 86 by pins 96. The proximal ends of arms 82 are pivotally attached to the distal ends of arms 84 and an intermediate part of a corresponding wing 52a,b,c,d by pins 118 (see FIGS. 4 and 6). The proximal ends of arms 84 are pivotally mounted to annular support 58 by pins 120 (FIG. 8) or steering wire 72 (FIG. 19), as described above. Hence, tension applied to the looped deployment wire 80 will cause the arms to buckle (FIG. 4) which in turn deploys the wings 52a,b,c,d outwardly. Deployment wire 80 is anchored at its proximal ends, preferably, to a multiply ribbed anchor 90 (FIG. 13) which mates with control mechanism 54 such that a calibrated force may be directly transmitted from control mechanism 54 to the tubular slide by squeezing a trigger 92 to effect a radial displacement of the wings, all while intraluminal fluid-flow is minimally impeded within the patient's vascular system. Deployment wire 80 is capable of transmitting compressive forces, and preferably has a diameter of 0.014 inches or less. Thus, when trigger 92 is released, the deployment wire moves axially toward the distal end of head 50 thereby towing the tubular slide to its rest position and radially recoiling the wings.

In contrast to balloon based devices, therefore, the direct transmission of a physical force from trigger 92 to head 50 causes the device of the present invention to operate substantially instantaneously without the delays associated with the filling of a balloon. The uniform radial separation of the wings under the direction of the mechanical linkage of tubular slide 86 and coupling arms 82, 84 avoids the risk of stent or graftstent rotation, a common problem with wrapped angioplasty balloon deployment designs.

A slot 98 (FIG. 4) in each wing 52 accommodates bifurcated lugs 94 and coupling arm 82 when the wings are recoiled. This allows for a more compact profile of head 50 for intraluminal delivery and removal after the surgical procedure is complete (see FIG. 2). Head 50 can be formed with a profile of approximately five millimeters which permits the introduction of stent 48 into smaller vascular systems than a conventional balloon-stent deployment design may facilitate.

Head 50 includes cylindrical initiator 88 for initiating the radial motion of the wings from their recoiled stance shown in FIG. 3. This makes it easier to fully deploy the wings 52a, b, c, d by applying tension to deployment wire 80. An initiator wire 78, which extends through the central lumen of initiator 88 is anchored to the initiator in a circumferential slot 100, and is used to axially slide the initiator with respect to the arms 84. Slot 100 is preferably formed with a pair of opposing holes 102 through which initiator wire 78 may be threaded and wrapped securely (see FIG. 7). A force applied to the proximal end of initiator wire 78 by control mechanism 54 slides initiator 88 with respect to guide wire 56. Advancement of initiator 88 toward the distal face of annular support 58 causes it to engage sloped surfaces 104 (shown by the dashed lines of FIG. 3) of the coupling arms 84. Preferably, the sloped surfaces 104 have a 15° pitch. Continued proximal movement of initiator 88 causes it to bear against the sloped surface of each arm 84. In response to this pressure, each coupling arm 84 buckles slightly about a pair of lugs 106, i.e. the distal portions of the coupling arms pivot slightly away from tubular slide 86 to initiate movement of each respectively coupled wing slightly radially outward. Coupling arms 82 similarly pivot about lugs 94 while tubular slide 86 is moved slightly toward the distal face of annular support 58. Advantageously, the portion of initiator 88 that bears against surface 104 is shaped as a frustrum so that frictional forces are minimized. Reduced frictional forces permit use of a thinner, more compact initiator wire 78. Preferably, initiator wire is 0.014 inches or less in diameter.

For certain types of stent or attachment devices where low radial forces are required, only one deployed means may be required.

After the initiator 88 has caused the arms 82, 84 to buckle slightly and the slide 86 has started to move, wings 52 can be fully radially displaced, as shown in FIG. 4, by advancing tubular slide 86 toward the distal face of annular support 58 by squeezing trigger 92 to apply tension to deployment wire 80.

In FIG. 9, head 50 is shown within a body lumen 108 with tubular slide 86 retracted toward the distal face of annular support 58, as by trigger 92, to bow coupling arms 82,84 outward and radially separate the wings. As the stent support surface separates with the radial motion of the wings, the stent deforms at four contact points 110a, 110b, 110c, and 110d. The stent is anchored to the walls of the body lumen when the wings have dilated substantially to the diameter of the body lumen. Thus, if body lumen 108 were the abdominal aortic artery, the wings would be dilated to approximately 35 to 40 mm. To firmly seat the stent in the body lumen, the wings are preferably recoiled and rotated so that the stent can be redistended at four other contact points. In FIG. 9, head 50 has been rotated approximately 45° and redistended to contact the body lumen at points 112a, 112b, 112c, and 112d, as shown by the dashed lines. Rotation and redistention may be repeated as many times as necessary to firmly seat the stent in the body lumen.

Each of the wings preferably has a stepped inner surface 116 to accommodate coupling arms 82, 84 (see FIG. 7). Each wing also has a primary rib 122 at a distal end and a secondary rib 124 at a proximal end. A recess 126 between the wings holds the stent in place.

Advantageously, head 50 and shaft 64 form a delivery system that can be preconfigured with a particular stent 48 or graftstent complex 44 of suitable length for a particular surgical procedure.

The extent of expansion of the stent is directly controlled by the travel of trigger 92 which governs tubular slide 86. This travel can be calibrated to a predetermined level of expansion, e.g., thirty-five min. Once expanded to the predetermined size, after re-evaluation of the prosthesis positioning, the stent can be immediately redilatated to a larger size without the introduction of a new deployment head 50 or a catheter exchange. The stent can be incrementally dilated to larger sizes on a moment-by-moment basis depending on real time fluoroscopic images and the surgeon's discretion as a function of the actual arterial dimensions instead of relying on estimated dimensions that are conventionally made prior to the procedure using an angiogram. This affords a decrease in blood loss during such redilation procedures and cuts down on the amount of time and cost involved with conventional procedures which could require multiple angioplasty catheter exchanges to redilate the stent.

In accordance with another object of the invention, the apparatus of the present invention may be used without stent 48 for native artery angioplasty. In such a procedure, head 50 would be advanced to the designated site within a patient's vascular system under fluoroscopic control in conventional manner by sliding the device over a separately inserted guide wire 56, as described above. Here, however, head 50 is advanced to the site of a stenosis at which time trigger 92 is squeezed to effect a radial displacement of wings 54a, b, c, d against the stenosis all while intraluminal fluid flow is minimally impeded within the patient's vascular system. As a result, any plaque or other deposit on the walls of a body lumen will be flattened by the radially displaced wings themselves.

In FIGS. 11-19, there is seen control mechanism 54 as may be used with head 50 and shaft 64. Several views are given so that the geometry of control mechanism 54 can be better appreciated.

Figure 16:
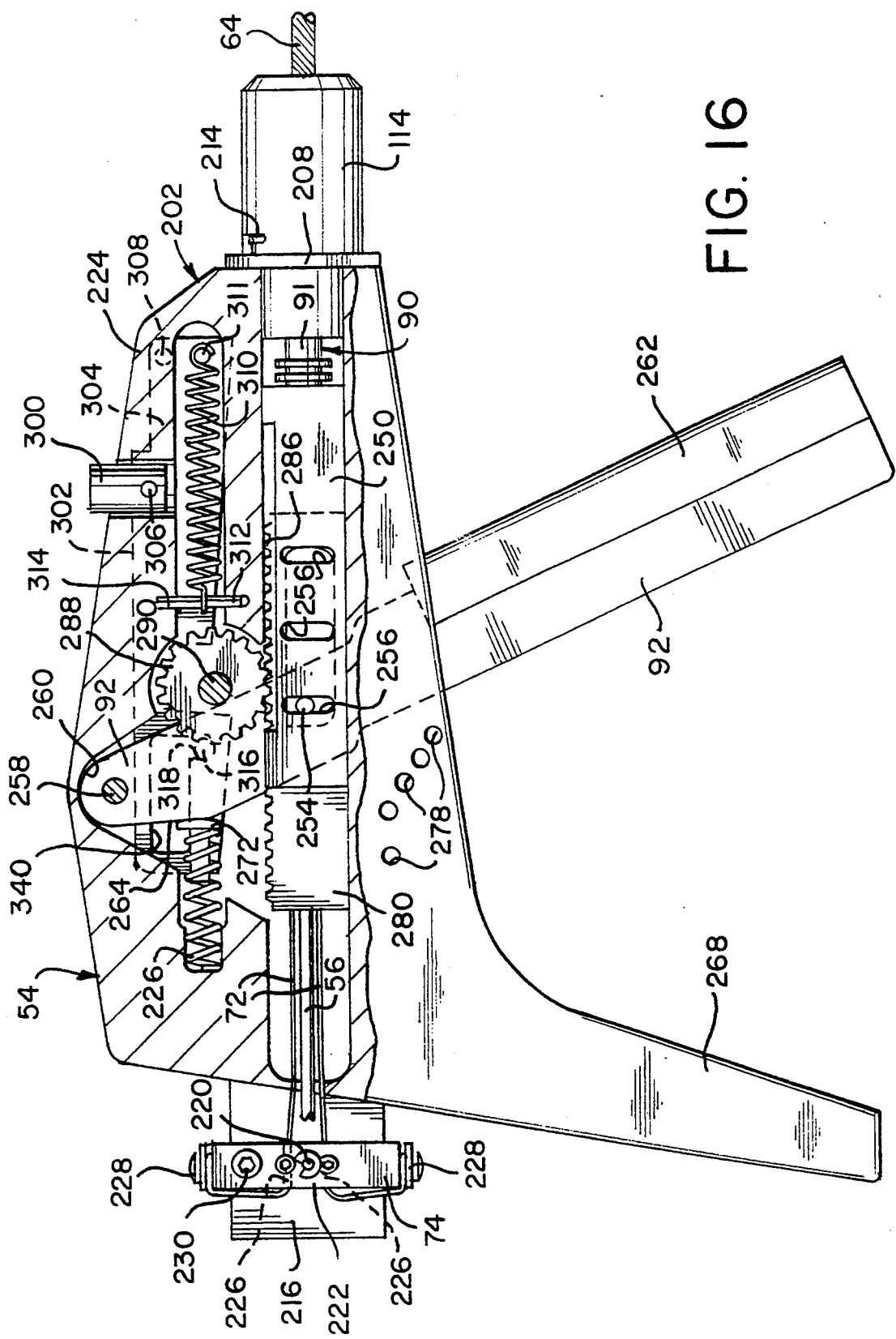
FIG. 16 is a partial cross-section of a second side of the actuator subassembly and the catheter mounting subassembly taken substantially along line 16—16 of FIG. 11.

The control mechanism comprises a catheter mounting subassembly 200 and an actuator subassembly 202 (FIGS. 11 and 13). The catheter mounting subassembly comprises a plate 204 which supports the rotatable nose cone 114, a multiply ribbed anchor 90 attached to the proximal end of the deployment wire 80, an anchor 242 attached to the proximal end of the initiator wire 78, and steering lever 74 attached to the proximal end of the steering wire 72. (FIG. 16). The catheter mounting subassembly mates with a first side 206 of actuator subassembly 202 to form an assembled control mechanism 54. A C-shaped retaining ring 208 is attached to the proximal end of plate 204 by a pair of screws 210 to unite mounting subassembly 200 with nose cone 114. The nose cone has a circumferential groove 212 (see FIG. 13) that permits it to be rotatably supported in retaining ring 208 to plate 204. It is desirable to have the nose cone rotatably supported in the catheter mounting subassembly so that head 50 can be rotated once located within a patient's body for redistending the stent at contact points other than where the stent is first distended. The nose cone is provided with a stop 214, as shown in FIG. 12, that limits rotation to approximately 360°. A click stop (not shown) may be provided at regular intervals, for example, 45°, to provide a tactile indication of the amount of rotation brought about by rotation of nose cone 114. Multiply ribbed anchor 90 has at its distal end a cylindrical sleeve 91 that is slideably mounded in an annular recess 115 in the proximal face of nose cone 114.

Attached by additional screws 211 to the distal end of plate 204 is an end plate 216 which supports steering lever 74 which is connected to the proximal ends of steering wire 72 (see FIG. 16). The steering lever is pivotally secured onto a pivot pin 220 with a locking washer 222 that is press fit onto pivot pin 220. Steering wire 72 is directed through a hole 226 in the steering lever to a clamping screw 228. After advancement to the site for deploying the stent or graftstent complex, the natural angle that head 50 assumes can be set by tightening a set screw 230. Alternatively, head 50 can be manually manipulated for advancement to the desired portion of the vascular system by rotating steering lever 74 with set screw 230 loosened.

FIGS. 14 and 15 show cross-sections of the mounting subassembly and actuator subassembly before and after control mechanism 54 is assembled, respectively. Assembly is facilitated by a peg 234 and a slot 232 complementarily formed on each of the mounting subassembly and actuator subassembly, as shown in FIG. 14, to guide the catheter mounting subassembly and actuator subassembly together. Shaft 64 is received in control mechanism 54 by means of catheter mounting subassembly 200 after the stent or graftstent complex has been loaded upon shaft 64 and delivered to the desired location within a patient's vascular system. Mounting subassembly 200 is then secured to actuator subassembly 202 to form a single mechanism as by screws 236, shown in FIG. 16, or by any other means to hold two components together. The mounting subassembly enables head 50 to be operated remotely by trigger 92, yet further provides an automatic calibration of the distention of the stent, as described below.

Advantageously, the travel of trigger 92 is calibrated to the radial motion of the wings so that dilation of the stent is certain and precise. Deployment wire 80, which is coupled at its distal end to tubular slide 86, is rigidly coupled at its proximal end to anchor 90 by a washer 238 and a nut 240 (see FIG. 13) so that a force applied to anchor 90 by trigger 92 is conveyed to tubular slide 86 to displace the wings and distend any stent 48 thereon. In similar manner, initiator wire 78 coupled at its distal end to initiator 88 is coupled at its proximal end to a spool-shaped anchor 242 by a washer 244 and a nut 246. A force applied to anchor 242 by actuating lever 248 is thus conveyed to initiator 88 to displace the wings slightly radially outward, as described above in connection with FIG. 3.

With further reference to FIGS. 14 through 16 and 18, trigger 92 is shown coupled to anchor 90 by a slotted yoke slide 250 terminated at the distal end in a yoke 252. Yoke 252 selectively engages multiply ribbed anchor 90 between any one of several ribs when the catheter mounting subassembly is assembled with the actuator subassembly (see FIG. 18). This is a self-zeroing control to account for cable bending, as more completely described in connection with the operation of the device. Thus, the actual set of ribs on anchor 90 to which yoke 252 engages is determined based on the orientation of shaft 64 in the patient's body. This ensures that the yoke 252 engages anchor 90 with the wings completely recoiled to provide the most compact profile achievable, yet permit the wings maintain a calibrated position relative to trigger 92. A link pin 254 attached to the trigger engages one of a plurality of vertical slots 256 in yoke slide 250 so that the travel of the trigger remains accurately calibrated to the force conveyed to anchor 90 which, in turn, governs the radial displacement or recoil of the wings. The trigger pivots on a pin 258 in an arcuate shaped milled recess 260 formed in second side 224 of actuator subassembly 202. As the trigger pivots on pin 258, link pin 254 travels in an arc along with the trigger. Link pin 254 draws yoke slide 250 linearly forwards and backwards in actuator subassembly 202 by engagement with vertical slots 256. Vertical slots 256 accommodate the arc traced by link pin 254 as it travels with the trigger while translating the pivotal motion of the trigger into the linear motion of yoke slide 250. This pivotal motion is in response to a force applied to a grasp handle 262 which may be provided to ensure a firm control over the trigger.

Between the trigger and yoke slide 250 is a rack 280 terminated at one end with a yoke 282. Rack 280 has an aperture 284 so that it can slide in actuator subassembly 202 without contacting pin 254 of trigger 92. Rack 280 has on a top margin thereof a set of teeth 286 that cooperate with a pinion gear 288 formed on one end of actuating lever 248. Actuating lever 248 pivots about a pin 290 between a pair of lever stops 292a,b (see FIG. 11 ). From FIGS. 16 and 17, it is seen that as the actuating lever 248 pivots from 292a to 292b, pinion gear 288 drives rack 280 in an opposite direction and tows anchor 242 therealong.

An edge 264 of trigger 92 is normally biased by a spring 266 into a forward position, away from a butt 268 of the actuator subassembly. Spring 266 is housed in a horizontal slot 270 and urges a disc 272 against edge 264 in resistance to any force applied to the trigger. As part of a safety mechanism, trigger 92 may include an aperture 274 for receiving a peg 276 from a corresponding hole in actuator subassembly 202. Peg 276 restrains the trigger from pivotal motion until removed from aperture 274. A set of peg holes 278 extending toward butt 268 is shown for limiting the motion of the trigger to the hole in which peg 276 has been placed. Advantageously, each of holes 278 is calibrated to the relative displacement of the wings so that holes 278 may be labeled, for example, 20, 24, 26, 28, 30, and so on, to provide a millimeter scale of the distention of the stent upon squeezing the trigger to a particular one of holes 278.

Figure 17:
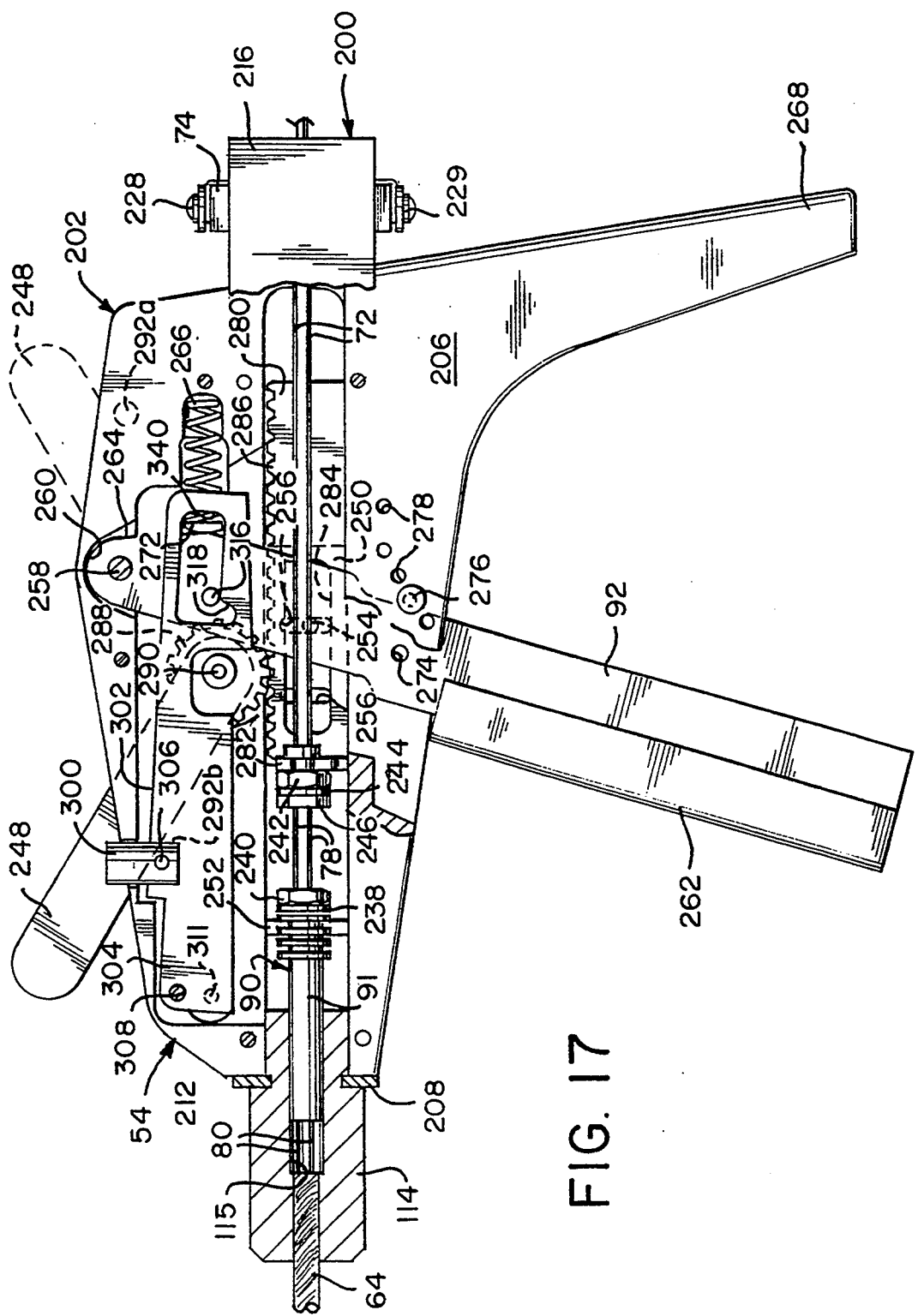
FIG. 17 is the same view as FIG. 13 showing the operation of a trigger and an actuating lever.

Control mechanism 54 includes a trigger lock mechanism that restrains the trigger from pivotal motion unless a button 300 on a top surface 302 of the control mechanism is first depressed. This button is attached to a lever lock 304 by a pivot 306 (FIGS. 16 and 17). The lever lock 304 pivots about a pivot pin 308 and is normally biased by a spring 310 into a locked position (see FIGS. 13 and 18). Spring 310 is connected between a pin 311 below pivot pin 308 on lever lock 304 and a post 312 disposed in a pair of slots 314 formed in actuator subassembly 202. A pin 316 (FIGS. 13 and 17) on the trigger 92 rests in a slot 318 formed in lever lock 304 when lever lock is in its locked position. So long as pin 316 is in slot 318 (FIGS. 13 and 16), the trigger cannot pivot and the wings will remain in a recoiled position. When the button is depressed, however, the lever lock pivots about pivot pin 308 and releases trigger pin 316 from slot 318. With the trigger pin released, it can travel freely within an aperture 340 formed in lever lock 304 while the trigger is being squeezed. Thus, trigger 92 radially displaces the wings by the coupling of the trigger to the wings by way of link pin 316, slotted yoke slide 250, yoke 252, multiply ribbed anchor 90, deployment wire 80, tubular slide 86, and coupling arms 82.

FIG. 19 shows a modification of the above described embodiment. There, a second ferrule 62' is formed on the proximal end of first ferrule 62. A pivot pin 60' pivotally couples the second ferrule to the first ferrule on the distal end of the shaft. The second ferrule is rotated 90° with respect to the first ferrule to increase the steerability of head 50. A second taut steering wire 72' is looped at its distal end through suitable holes formed transverse to pin 60' at the proximal end of first ferrule 62. Preferably, head 50 is universally steerable by manipulating steering wires 72,72'. Multilumen catheter 68 has at least one lumen for a wire coupled to the second ferrule of this modified embodiment. In addition, second ferrule 62' is press fit onto the distal end of elongate flexible shaft 64.

Prior to performing an operation using the device of the present invention, a surgeon first determines the nature of the atherosclerosis, that is whether there is a stenosis or aneurysm. This may conventionally be determined by means of an angiogram. In the case of a stenosis, native artery angioplasty can be performed by using the device, in the manner described below, without a stent 48a. Alternatively, a stent 48a may be used to support the walls of body lumen 108 from constricting. On the other hand, in the case of an aneurysm, a graftstent complex 44 of suitable length is required to bypass an aneurysm. The angiogram further provides the surgeon with an indication of the lumen width in the region surrounding the stenosis or aneurysm. This indication of lumen width is advantageously used to set the maximum travel of trigger 92 by setting peg 276 in an appropriate one of calibrated holes 278.

Once the amount of distention is known, a suitable stent or stentgraft complex may be selected. The entire graftstent 44 can be prefabricated and mounted on head 50 in a manner ready for connection to actuator subassembly 202 and subsequent deployment; a surgeon need only specify the length of graft 46 necessary to bypass an aneurysm and the maximum distention desired of stent 48a. The length of the aneurysm is determined during the angiogram.

In accordance with the Seldinger method, a guide wire 56 is advanced within a conventional guide catheter or sheath through a patient's vascular system to a position beyond the stenosis or aneurysm. Head 50 at the distal end of the elongate flexible shaft 64 is then advanced over the proximal end of guide wire until it reaches the site of the stenosis or aneurysm. A fluoroscopic image of the patient's abdominal cavity may assist locating head 50 relative to the designated site. Where head 50 is formed of plastic or epoxy materials, it is advantageously provided with a radiopaque portion to assist in the fluoroscopic alignment process. At the distal end of shaft 64 is an unmounted catheter mounting subassembly 200.

Where a stent or stentgraft complex is to be used, it is loaded upon head 50 at the distal end of shaft 64 prior to being inserted into the patient. A sheath 330 is placed over the prosthesis for smooth delivery to the site of a narrowing or an aneurysm.

All while head 50 is being advanced over the guide wire and through the patient's vascular system, steering lever 74 may be manipulated by the surgeon so that catheter 64 successfully negotiates the tortious and twisty arteries encountered. Once head 50 has reached the designated site, the steering lever can be set by screw 230 so that head 50 will retain its naturally assumed angle during the displacement of wings 54a, b, c, and d. Once head 50 has been advanced to the designated site, shaft 64 will likely have bends in it between its distal and proximal ends. These bends will pull on the initiator and deployment wires 78, 80 which in turn will axially reposition anchors 90, 242 with respect to nose cone 114 at the proximal end of shaft 64. Nevertheless, the calibration of holes 278 remains intact because deployment anchor 90 always engages yoke 252 with wings 54 in a completely recoiled stance when the catheter mounting subassembly is joined with the actuator subassembly. This is due to the multiply ribbed surface of anchor 90 which engages yoke 252 regardless of its axial position relative to yoke 252 at the moment when the subassemblies are joined. In effect, this provides a built-in self-zeroing feature so that regardless of the tortuosity of the vasculature the head will be in its closed position when the stent is properly located.

Once head 50 has been advanced to the designated site, the catheter mounting subassembly and the actuator subassembly are joined to form an assembled control mechanism 54. The sheath, when present, is withdrawn by a sheath retractor (not shown) for displacement of the wings.

The actuating lever 248 is then advanced from lever stop 292a to 292b to draw initiator 88 toward annular support 58 and to separate the wings slightly radially. The trigger lock button 300 can then be released and the trigger 92 compressed toward butt 268 to draw tubular slide 86 toward annular support 58 and displace the wings. As the wings displace radially outward, the distance between each wing increases and the stent, supported on the wings, assumes a radially expanded circumstance. The trigger 92 may be squeezed until it hits peg 276 (FIG. 17) at which point stem 48a may be expanded sufficiently to anchor it to body lumen 108, at least according to the angiogram data collected prior to the operation. Stent 48a can be incrementally dilated to larger sizes by removing peg 276 and squeezing trigger 92 beyond the hole 278 which peg 276 formerly occupied. This may be done on a moment-by-moment basis depending on real time fluoroscopic images and the surgeon's discretion as a function of the actual arterial dimensions. When the trigger is released, spring 266 urges the trigger to its rest position which conveys a pushing force through yoke 252 and deployment wires 80 to tubular slide 86. When tubular slide 86 is pushed away from annular support 58, the wings return to a radially recoiled stance and stent 48a retains its radially expanded circumstance.

The direct transmission of a physical force from trigger 92 to head 50 permits rapid displacement and recoil of the wings. Displacement and recoil can be performed in virtually less than a second, as compared to the time required for balloon dilatation which may be as much as twenty to thirty seconds and sometimes up to a minute. Relative to balloon based devices, therefore, the present invention operates substantially instantaneously without the delays associated with filling a balloon. All the while, intraluminal fluids flow between the radially displaced wings. Additionally, because the wings uniformly separate radially under the direction of the mechanical linkage of tubular slide 86 and coupling arms 82, 84, there is no risk of stent or graftstent rotation, a common problem with wrapped angioplasty balloon deployment designs.

Head 50 can then be rotated so that stent 48a can be redilated at contact points other than where it has already been dilated. This procedure better secures the stent to the body lumen. Rotation is effected by rotating nose cone 114. This turns shaft 64 and head 50 and thereby angularly repositions wings 54 with respect to the body lumen 108. Trigger 92 can then be squeezed to distend stent 48a at a new set of contact points. This procedure may be repeated as many times as desired until stent 48a is firmly seated. Alternatively, rotation of head 50 and relocation of wings 54 aid in the procedure of native artery angioplasty in the absence of a stent by flattening plaque and any other deposit on the body lumen.

Where a stentgraft complex is to be deployed in a patient, a stent 48b must be deployed once stent 48a has been deployed. Shaft 64 is withdrawn, preferably with the assistance of a fluoroscopic image of the patient's abdominal cavity, until head 50 is surrounded by undistended stent 48b. As shaft 64 is being withdrawn, stent 48b will pass over secondary rib 124 and become seated on the support surface when one margin of stent 48b abuts primary rib 122. As noted above, where head 50 is formed of plastic or epoxy materials, it is advantageously provided with a radiopaque portion to assist in the fluoroscopic alignment process. As above, the actuating lever 248, button 300, and trigger 92 are used to deploy stent 48b. After deployment of stent 48b, when present, shaft 64 and guide wire 56 can be withdrawn from the patient's vascular system. Thus, multiple stents 48a and 48b may be deployed with a single introduction into a patient's vascular system.

Each of wire 72, 78, and 80 is preferably stainless steel. Head 50 may be produced in a disposable or non-disposable fashion. Where head 50 is to be disposed of after usage, at least wings 52, tubular slide 86, coupling arms 82, 84, initiator 88, and annular support 58 may be compression molded or extruded from an epoxy material or plastic. The same components of head 50 listed above are advantageously formed of stainless steel where head 50 is intended to be reused in a subsequent procedure. One skilled in the art would recognize that the choice of materials for the head affects the radiopacity of the head. Thus, an epoxy or plastic head would be radiolucid as compared to a stainless steel head which would be radiopaque.

Sheath 330 may be of a plastic or teflon material. Presently, the materials most commonly used as prosthetic arteries are PTFE ("GORTEX") and polyester ("DACRON"), however, other suitable grafts may be used with this device. No single prosthetic material has surfaced as being superior to others. Excellent results may be also had using a patient's own accessory vein, albeit with more imposition to the patient.

From the foregoing description, it will be clear that the present invention may be embodied in other specific forms without departing from the spirit or essential characteristics thereof. Thus, for example, while the embodiments discussed above described pivotal couplings at 62 and 62', a rough surfaced ball could define one end of annular support 58 for universal motion at the end of shaft 64. This ball could be displaceably seated so that wires 72 frictionally hold head 50 at any angle naturally assumed by the placement of head 50 within a particular segment of body lumen 108. Advantageously, lever lock 304 is coupled to anchor 90 so that when button 300 is depressed, head 50 is frictionally seated and wings 52 are simultaneously radially displaced. The presently disclosed embodiments are therefore to be considered in all respects as illustrative and not restrictive, the scope of the invention being indicated by the appended claims, and not limited to the foregoing description.

The invention is intended for use in deploying stems and attachment devices, i.e. devices which may be attached to a body lumen such as an artery, for example to secure a graft in place. As used herein, the term "stem" is intended to also include such attachment devices. The invention can be used with any radially expandable stem, including stems which are partially self-expanding.

Although the invention is shown with one head deploying a single stem at a time, it is contemplated that two heads on a single device may simultaneously deploy two spaced apart stents.

We claim:

1. In combination with an expandable prosthesis, an apparatus for intraluminal delivery and deployment of the expandable prosthesis at a site within a body lumen, comprising:
   a support for supporting the expandable prosthesis while being delivered to the site within the body lumen; and
   a radially displaceable mechanical linkage connected to said support for radially displacing said support, said linkage adapted to deploy the expandable prosthesis when said linkage is displaced radially outward, said linkage permitting continuous fluid flow within the body lumen while the expandable prosthesis is being deployed.

2. An apparatus as in claim 1, further comprising axially moveable control means coupled to said linkage for remotely controlling said linkage.

3. An apparatus as in claim 2, further comprising means to normally bias said control means in an axially distal position such that said linkage is normally in a recoiled stance for delivery and withdrawal of said apparatus from the lumen, said axially moveable control means transmitting one of an expansion and compression force to said linkage.

4. In combination with a stem, an apparatus at a predetermined location on a catheter for intraluminally deploying the stent, comprising:
   a member, said member being movably mounted with respect to the catheter;
   a deployment wire having a distal end fixedly coupled to said member for axially moving said member with respect to the catheter;
   a plurality of wings surrounding said member to form a support surface for the stent; and
   a linkage for linking said wings to said member and the catheter, said linkage causing said wings to displace radially outward when said member is moved axially by said deployment wire in a first direction and displace radially inward when said member is moved axially by said deployment wire in a second direction.

5. An apparatus as in claim 4, further comprising a rigid portion axially mounted with respect to said guide wire, said rigid portion being coupled to said wings.

6. An apparatus as in claim 5, further comprising a plurality of first and second arms, each of said wings being linked to said member by at least one of said first arms and to said rigid portion by at least one of said second arms.

7. An apparatus as in claim 6, wherein each of said wings is pivotally linked to said member by at least one of said first arms and to said rigid portion by at least one of said second arms.

8. An apparatus as in claim 6, wherein said wings have a stepped surface opposite said support surface, said stepped surface permitting the apparatus to assume a compact radial profile.

9. An apparatus as in claim 6, further comprising initiating means axially movably mounted with respect to the guide wire for initiating displacement of said wings.

10. An apparatus as in claim 9, further comprising an initiating wire fixedly coupled to said initiating means for axially moving said initiating means with respect to the guide wire.

11. An apparatus as in claim 10, further comprising an actuator coupled to said initiating wire such that movement of said actuator causes said initiating means to move axially in one of said first and second directions.

12. An apparatus as in claim 9, wherein each of said second arms has a distal portion free of contact of said initiating means and a proximal portion that engages said initiating means when said initiating means moves axially in said first direction.

13. An apparatus as in claim 12, wherein said proximal portion of each of said second arms has a sloped edge which gradually engages said initiating means when said initiating means moves axially in said first direction, whereby each of said wings is radially displaced from said member and the stent supported on said wings is radially expanded.

14. An apparatus as in claim 13, wherein said sloped edge is 15°.

15. An apparatus as in claim 5, further comprising a steering wire fixedly coupled at a distal end to said rigid portion.

16. An apparatus as in claim 15, further comprising a steering control coupled to a proximal end of said steering wire.

17. An apparatus as in claim 5, further comprising a catheter shaft articulately mounted at a distal end thereof to said rigid portion.

18. An apparatus as in claim 17, wherein said articulately mounted rigid portion is universally connected to said catheter shaft.

19. An apparatus as in claim 17, wherein said articulately connected rigid portion is hingeably connected to said catheter shaft.

20. An apparatus as in claim 17, further comprising a trigger mechanism, said catheter shaft being rotatably mounted at a proximal end thereof to said trigger mechanism, said trigger mechanism being coupled to a proximal end of said deployment wire.

21. An apparatus as in claim 20, further comprising a trigger housing and a peg for insertion into said housing, said housing and peg defining the movement of said mechanism, said trigger mechanism being movable within said housing from a rest position to said peg, said wings displacing radially outward as said trigger mechanism moves toward said peg.

22. An apparatus as in claim 21, wherein said housing has a plurality of holes for receiving said peg, each of said holes corresponding to a calibrated relative displacement of said wings.

23. An apparatus as in claim 22, wherein said calibrated relative displacement of said wings is predetermined.

24. An apparatus as in claim 4, wherein said deployment wire is terminated at a proximal end with a slotted portion.

25. An apparatus as in claim 24, further comprising a trigger mechanism, said trigger mechanism engaging said slotted portion such that movement of said trigger mechanism causes said member to move axially with respect to the guide wire in one of said first and second directions and causes each of said wings to displace radially.

26. An apparatus as in claim 25, further comprising a trigger housing and a peg for insertion into said housing, said housing and peg defining the movement of said mechanism, said trigger mechanism being movable within said housing from a rest position to said peg, said wings displacing radially outward as said trigger mechanism moves toward said peg.

27. An apparatus as in claim 26, wherein said housing has a plurality of holes for receiving said peg, each of said holes corresponding to a calibrated relative displacement of said wings.

28. An apparatus as in claim 27, wherein said calibrated relative displacement of said wings is predetermined.

29. In combination with a stent, an apparatus at a predetermined location on a catheter for intraluminally deploying the stent, comprising:
a member, said member being movably mounted with respect to the catheter;
a wire having a distal end coupled to said member for axially moving said member with respect to the catheter;
a plurality of first and second arms;
a plurality of wings surrounding said member to form a support surface for the stent, each of said wings being pivotally linked to said member by at least one of said first arms; and
a rigid portion connected to the catheter, each of said wings being pivotally linked to said rigid portion by at least one of said second arms, whereby a force applied to said wire causes said wings displace radially outward when said member is moved axially by said wire in a first direction and displace radially inward when said member is moved axially by said wire in a second direction.

30. An apparatus as in claim 29, further comprising initiating means axially movably mounted with respect to the guide wire for initiating displacement of said wings.

31. An apparatus at a predetermined location on a catheter for expanding a graft, stent, or stenosed body lumen or the like, comprising:
a member, said member being movably mounted with respect to the catheter;
a deployment wire having a distal end coupled to said member for axially moving said member with respect to the catheter;
a plurality of wings surrounding said member;
a linkage for linking said wings to said member and the catheter and for providing a force sufficient to expand the graft, stent, stenosed body lumen or the like;
initiating means axially movably mounted with respect to the catheter for initiating displacement of said wings; and
an initiating wire fixedly coupled to said initiating means for axially moving said initiating means with respect to the catheter.

32. An apparatus as in claim 31, further comprising an actuator coupled to said initiating wire such that movement of said actuator causes said initiating means to move axially with respect to the catheter.

33. An apparatus at a predetermined location on a catheter for expanding a graft, stem, or stenosed body lumen or the like, comprising:
a member, said member being movably mounted with respect to the catheter;
a deployment wire having a distal end coupled to said member for axially moving said member with respect to the catheter;
a plurality of wings surrounding said member;
a linkage for linking said wings to said member and the catheter and for providing a force sufficient to expand the graft, stent, stenosed body lumen or the like;
a rigid portion axially mounted with respect to said catheter, said rigid portion being coupled to said wings; and
a plurality of first and second arms, each of said wings being linked to said member by at least one of said first arms and to said rigid portion by at least one of said second arms.

34. An apparatus as in claim 33, further comprising initiating means axially movably mounted with respect to the catheter for initiating displacement of said wings, each of said second arms having a distal portion free of contact of said initiating means and a proximal portion that engages said initiating means when said initiating means moves axially in said first direction.

35. An apparatus at a predetermined location on a catheter for expanding a graft, stent, or stenosed body lumen or the like, comprising:
- a member, said member being movably mounted with respect to the catheter;
- a deployment wire having a distal end coupled to said member for axially moving said member with respect to the catheter;
- a plurality of wings surrounding said member;
- a linkage for linking said wings to said member and the catheter and for providing a force sufficient to expand the graft, stent, stenosed body lumen or the like;
- a rigid portion axially mounted with respect to said catheter, said rigid portion being coupled to said wings; and
- a steering wire fixedly coupled at a distal end to said rigid portion.

36. An apparatus as in claim 35, further comprising a steering control coupled to a proximal end of said steering wire.

37. An apparatus at a predetermined location on a catheter for expanding a graft, stent, or stenosed body lumen or the like, comprising:
- a member, said member being movably mounted with respect to the catheter;
- a deployment wire having a distal end coupled to said member for axially moving said member with respect to the catheter;
- a plurality of wings surrounding said member;
- a linkage for linking said wings to said member and the catheter and for providing a force sufficient to expand the graft, stent, stenosed body lumen or the like;
- initiating means axially movably mounted with respect to the catheter for initiating displacement of said wings; and
- a rigid portion axially mounted with respect to said catheter, said rigid portion being coupled to said wings;
- wherein said rigid portion is articulately mounted at a distal end of the catheter.

38. An apparatus as in claim 37, further comprising a trigger mechanism, said catheter being rotatably mounted at a proximal end thereof to said trigger mechanism, said trigger mechanism being coupled to a proximal end of said deployment wire.

39. An apparatus at a predetermined location on a catheter for expanding a graft, stem, or stenosed body lumen or the like, comprising:
- a member, said member being movably mounted with respect to the catheter;
- a deployment wire having a distal end coupled to said member for axially moving said member with respect to the catheter and a proximal end terminated with a slotted portion;
- a plurality of wings surrounding said member; and
- a linkage for linking said wings to said member and the catheter and for providing a force sufficient to expand the graft, stent, stenosed body lumen or the like.

40. An apparatus as in claim 39, further comprising a trigger mechanism, said trigger mechanism engaging said slotted portion such that movement of said trigger mechanism causes said member to move axially with respect to the catheter in one of said first and second directions and causes each of said wings to displace radially.

41. A method for intraluminally implanting a prosthesis disposed on a mechanical support at a predetermined location on a catheter which has been inserted into a body passageway, comprising the steps of:
- transmitting a radially, outwardly directed displacement force substantially instantaneously to the support from a control mechanism, said support being displaced radially outwardly to an expanded stance such that the prosthesis contacts the body passageway;
- transmitting a radially, inwardly directed displacement force substantially instantaneously to the support from a control mechanism, said support being displaced radially inwardly to a recoiled stance less than the diameter of the body passageway while leaving the prosthesis in contact the body passageway; and
- permitting fluid flow while transmitting either of said radially, outwardly directed displacement force or said radially, inwardly directed displacement force.

42. A method as in claim 41, wherein each of the steps of transmitting a radially directed displacement force includes the step of directly translating an axial force from the control mechanism into a radial force at the distal end of the catheter.

43. A method as in claim 41, wherein each of the transmitted displacement forces is calibrated to the displacement of the support such that a prosthesis is expanded to a predetermined diameter.

44. A method as in claim 41, including the additional step of guiding the prosthesis upon the support to a designated site within the body passageway.

45. A method as in claim 41, including the additional step of disposing the prosthesis upon a mechanical support.

* * * * *